United States Patent [19]
Florent et al.

[11] 4,189,349
[45] Feb. 19, 1980

[54] α,δ-DIAMINOACID AND ITS LACTAM

[75] Inventors: Jean Florent, Boulogne-Billancourt; Jean Lunel, Paris; Denise Mancy, Charenton, all of France

[73] Assignee: Rhone-Poulenc Industries, Paris, France

[21] Appl. No.: 834,551

[22] Filed: Sep. 19, 1977

[51] Int. Cl.$^2$ .................................................. C12D 9/14
[52] U.S. Cl. ...................................... 435/87; 435/106; 536/26; 435/886
[58] Field of Search ............................ 195/28 N, 80 R

[56] References Cited
U.S. PATENT DOCUMENTS

| | | | |
|---|---|---|---|
| 3,337,530 | 8/1967 | Hanze | 195/28 N |
| 3,987,030 | 10/1976 | Suzuki et al. | 195/28 N |

Primary Examiner—Alvin E. Tanenholtz
Attorney, Agent, or Firm—Stevens, Davis, Miller & Mosher

[57] ABSTRACT

The new antifungal agents 32232 RP and 35391 RP having the probable formulae:

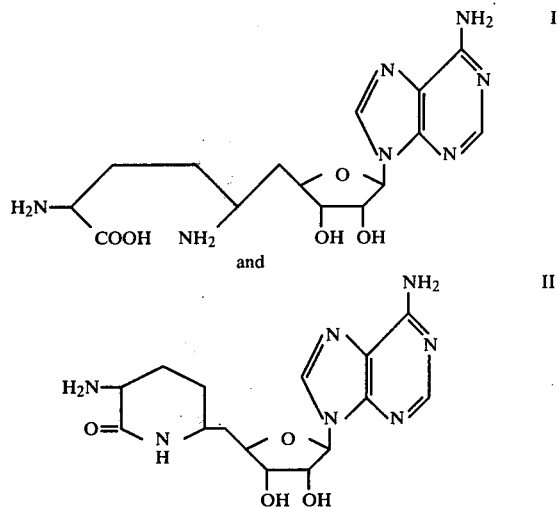

respectively, are prepared by cultivating the hitherto unknown microorganism *Streptomyces incarnatus* DS 26068 (NRRL 8089), under aerobic conditions in an aqueous nutrient medium to obtain 32232 RP which can be converted into the lactam 35391 RP.

10 Claims, 7 Drawing Figures

α,δ-DIAMINOACID AND ITS LACTAM

This invention relates to a new α,δ-diaminoacid hereinafter designated by the number 32232 RP, which probably corresponds to the formula:

in the form of its internal salt, its addition salts with acids and its salts with alkali metals or alkaline earth metals, and the corresponding lactam, hereinafter designated by the number 35391 RP, which probably corresponds to the formula:

and its addition salts with acids, to processes for their preparation and compositions containing them.

32232 RP and 35391 RP are of particular interest because of their activity on fungi and yeasts. 32232 RP, in the form of the internal salt, is characterised by the following physical properties:
Appearance: white amorphous powder.
Solubility: easily soluble in water, very slightly soluble in methanol and in dimethylformamide and virtually insoluble in acetone (according to the French Pharmacopoeia).
Melting point: (determined on a Maquenne block) + 281° C.

The structure of 32232 RP was determined on the basis of the following results:
Percentage composition: about C=48.0% H=5.8% O=21.0% N=25.2%: (theory: C=47.23% H=6.07% O=20.97% N=25.70%).
Osmometry: the molecular weight, determined by osmometry in water at 45° C., is between 330 and 470.
Potentiometric titration: potentiometric titration of an aqueous solution of 32232 RP by means of 0.1M hydrochloric acid shows the presence of a basic group of which the apparent $pK_a$ is 8.1. The potentiometric equivalent is about 390.

The potentiometric titration of an aqueous solution of 32232 RP by means of 0.1M sodium hydroxide solution shows the presence of a weak acid group of which the apparent pKa is 9.8. The potentiometric equivalent is about 400.

The potentiometric titration of a solution of 32232 RP in acetic acid by means of 0.01M perchloric acid in acetic acid shows the presence of a basic equivalent of about 130. For a molecular weight of 390 this value is compatible with the presence of 3 basic groups per molecule.

Figure 1:
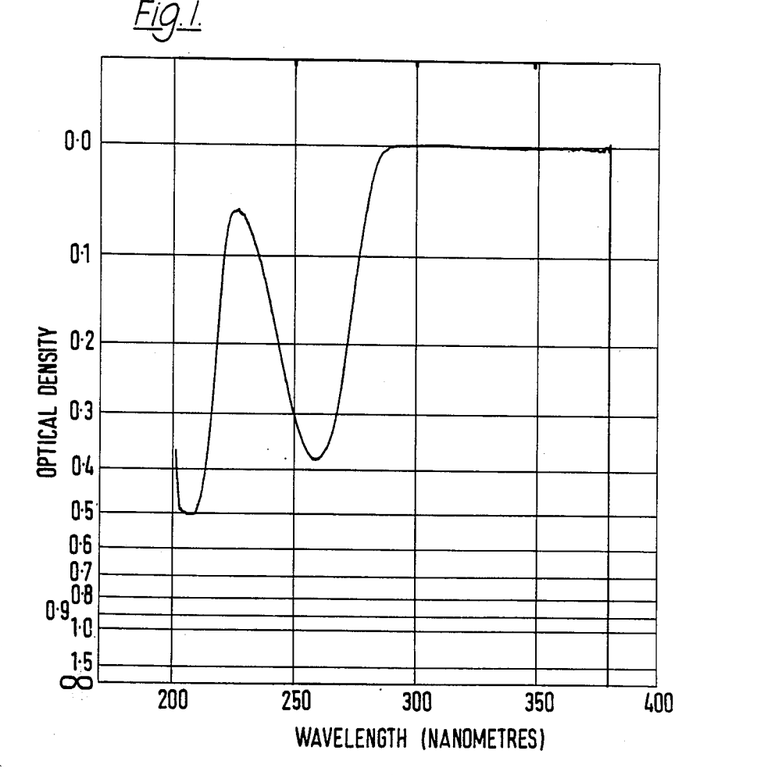

Ultra-violet spectrum: determined using a solution of 10.35 mg./l. in a phosphate buffer at pH 7 (0.1 M in respect of phosphate ions).

32232 Rp shows an absorption maximum at 258 nm ($E_{1\ cm}^{1\%} = 365$).

The spectrum is shown in FIG. 1 of the accompanying drawings.

Figure 2:
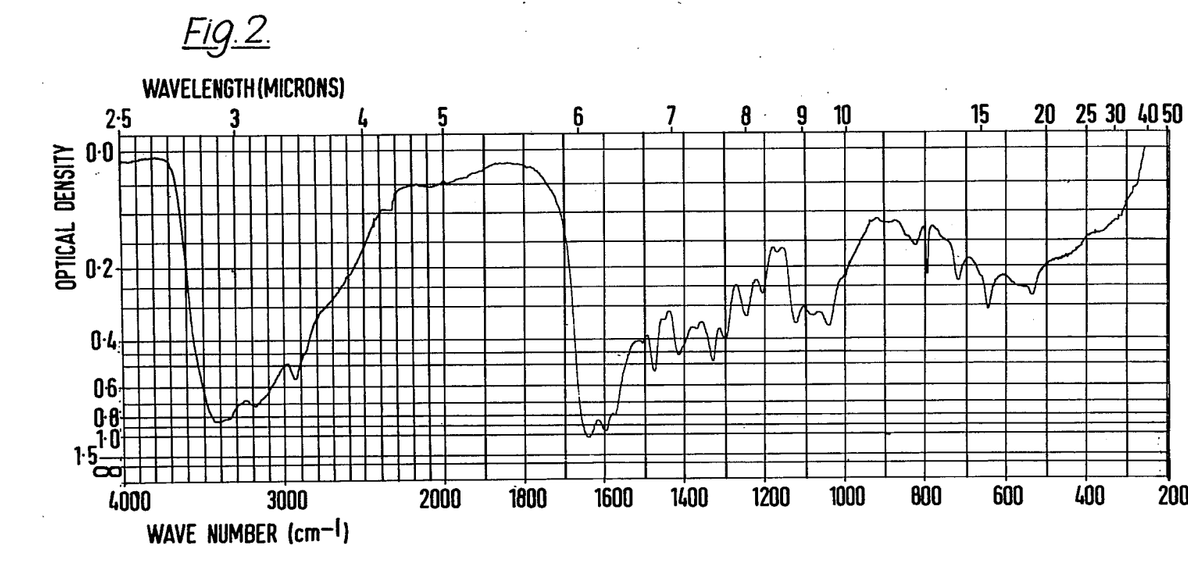

Infra-red spectrum: (determined on tablets of a mixture with KBr).

This spectrum is shown in FIG. 2, in which the abscissae give the wavelengths expressed in microns (upper scale) and the wave numbers in cm$^{-1}$ (lower scale), and the ordinate gives the optical density.

The principal infra-red absorption bands of 32232 RP, expressed in wave numbers (cm$^{-1}$), are given in Table I which follows:

TABLE I

| | | | |
|---|---|---|---|
| 3420 vs | 1640 vs | 1300 m | 825 m |
| 3350 sh | 1595 s | 1245 m | 795 m |
| 3270 sh | 1570 s | 1205 m | 760 sh |
| 3180 s | 1505 w | 1170 w | 720 m |
| 3090 sh | 1475 m | 1125 m | 665 sh |
| 2930 m | 1455 sh | 1080 m | 645 m |
| 2870 sh | 1415 m | 1040 m | 575 sh |
| 2700 sh | 1400 sh | 1010 sh | 535 m |
| 2340 sh (CO$_2$) | 1370 w | 900 vw | 440 sh |
| 2100 vw | 1330 m | 845 sh | | vs = very strong
w = weak
s = strong
vw = very weak
m = medium
sh = shoulder

Figure 3:
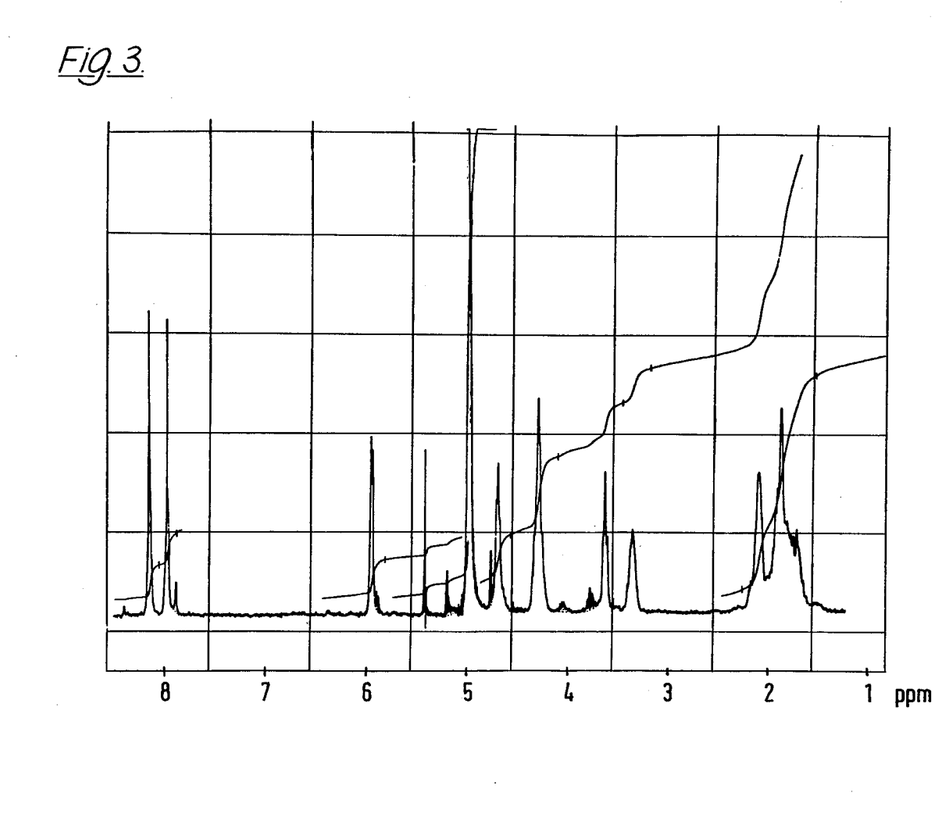

Nuclear magnetic resonance spectrum of the proton in heavy water: This spectrum, which is shown in FIG. 3, was recorded on a CAMECA TSN-250 spectrometer at a frequency of 250 MHz, using a solution of 50 mg/cc in heavy water. It exhibits the following characteristics (the chemical shifts are counted positively in p.p.m. towards the weak fields, relative to TMS used as an external standard):

| Chemical shift in p.p.m. | Form of the signal; coupling constant (J) and number of protons |
|---|---|
| 1.6 to 2.0 | multiplet (4 H) |
| 2.0 to 2.2 | multiplet (2 H) |
| 3.36 | multiplet (1 H) |
| 3.64 | multiplet (1 H) |
| 4.30 | multiplet (2 H) |
| 4.72 | double doublet, J = 4 Hz and 4 Hz (1 H) |
| 5.96 | doublet, J = 4 Hz (1 H) |
| 7.98 | singlet (1 H) |
| 8.16 | singlet (1 H) |

Figure 4:
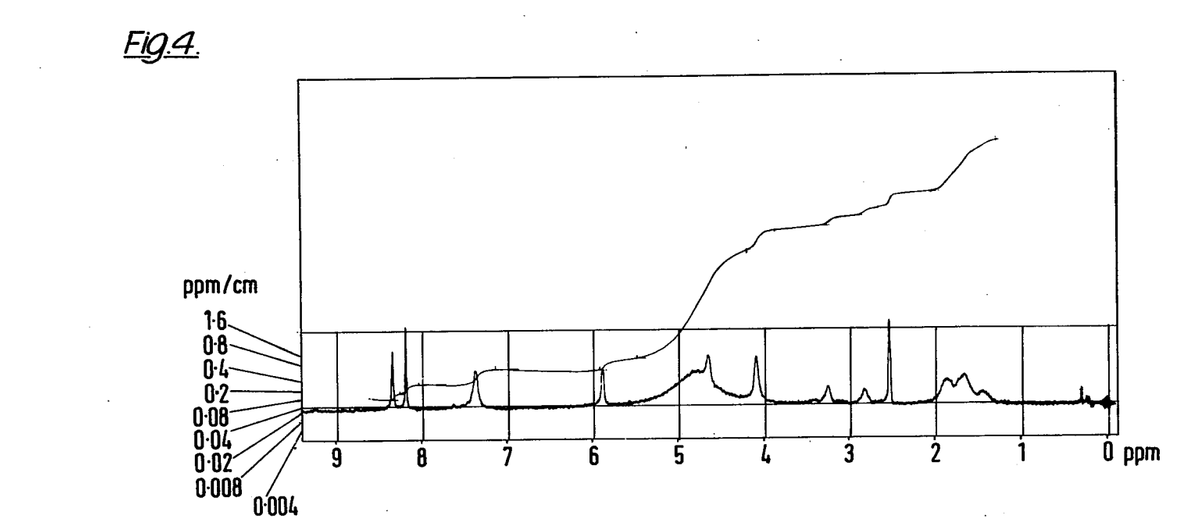

According to this spectrum, the antibiotic agent 32232 RP contains 14 non-exchangeable protons.
Nuclear magnetic resonance spectrum of the proton in hexadeuterated dimethylsulphoxide: This spectrum, which is shown in FIG. 4, was recorded on a CAMECA TSN-250 spectrometer at a frequency of 250 MHz using a solution of 44 mg/cc in hexadeuterated dimethylsulphoxide. It exhibits the following characteristics (the chemical shifts are counted positively in p.p.m. towards the weak fields, relative to TMS used as an external standard):

| Chemical shift in p.p.m. | Form of the signal; coupling constant (J) and number of protons |
| --- | --- |
| 1.3 to 2.05 | hump (6H) |
| 2.52 | quintuplet |
| 2.82 | hump (1H) |
| 3.24 | hump (1H) |
| 4.09 | hump (2H) |
| 4.2 to 5.4 | hump ⎤ |
|  |  ⎬ (13 H) |
| 4.64 | multiplet ⎦ |
| 5.88 | doublet, J = 4.5 Hz (1H) |
| 7.37 | hump (2 H) |
| 8.18 | singlet (1 H) |
| 8.34 | singlet (1 H) |

Nuclear magnetic resonance spectra of $^{13}C$ in heavy water: These spectra, which were recorded on a CAMECA TSN-250 spectrometer at a frequency of 62.86 MHz, using a solution in heavy water containing a trace of dioxan used as an internal standard, exhibit the characteristics which are summarised in the following Table (the chemical shifts are counted positively towards the weak fields from TMS; dioxan, used as an internal standard, shows, in the completely uncoupled spectrum, a singlet recorded at 66.59 ppm. relative to TMS):

| Chemical shift in p.p.m. relative to TMS | Form of the signal and coupling constant $^1J_{13C-H}$ in the non-uncoupled spectrum |
| --- | --- |
| 28.2 | triplet, J = 115.5 Hz |
| 30.1 | triplet, J = 114.4 Hz |
| 36.7 | triplet, J = 126.6 Hz |
| 48.4 | doublet, J = 143.4 Hz |
| 55.0 | doublet, J = 143.4 Hz |
| 66.59 | dioxan |
| 73.3 | doublet, J = 149.5 Hz |
| 73.5 | doublet, J = 151.0 Hz |
| 80.3 | doublet, J = 149.5 Hz |
| 88.3 | doublet, J = 167.9 Hz |
| 118.3 | singlet |
| 139.7 | doublet, J = 215 Hz |
| 148.0 | singlet |
| 152.3 | doublet, J = 203 Hz |
| 154.8 | singlet |
| 177.1 | singlet |

$^{13}C$ Nuclear magnetic resonance spectrum in hexadeuterated dimethylsulphoxide: This spectrum was recorded on a WH 90 Bruker spectrometer at a frequency of 22.63 MHz using a solution of 133 mg/cc in hexadeuterated dimethylsulphoxide. It exhibits the following characteristics (the chemical shifts are measured positively towards the weak fields relative to the hexadeuterated dimethylsulphoxide taken as the internal standard at 39.5 p.p.m. from TMS, and expressed in p.p.m. relative to TMS taken as zero):

| Chemical shift in p.p.m. relative to TMS | Form of the signal in the spectrum recorded in off-resonance |
| --- | --- |
| 28.3 | triplet |
| 32.7 | triplet |
| about 39.5 | signal masked by hexadeuterated dimethylsulphoxide |
| 47.8 | doublet |
| 54.2 | doublet |
| 73.2 | doublet |
| 73.6 | doublet |
| 80.7 | doublet |
| 87.8 | doublet |
| 118.8 | singlet |
| 139.5 | doublet |
| 148.9 | singlet |
| 152.3 | doublet |
| 155.6 | singlet |
| 172.1 | singlet |

According to these spectra, the anti-fungal agent 32232 RP contains 15 carbon atoms which can be subdivided into 4 quaternary carbon atoms, 8 tertiary carbon atoms (CH) and 3 secondary carbon atoms ($CH_2$).

Methanolysis in the presence of hydrogen chloride: The methanolysis of 32232 RP in the presence of hydrogen chloride shows the presence of adenine in the molecule of 32232 RP.

Chromatographic migrations: 32232 RP can be characterised by ascending chromatography on a thin layer of fluorescent silica gel (254 nm) using various mixtures of solvents. After development, the chromatograph is examined at 254 nm or is developed by spraying with ninhydrin in a mixture of acetone (20 cc) and acetic acid (1 cc); after heating, 32232 Rp gives a mauve colour. The development mixtures are:

Methanol/1,2-dichloroethane/11 N ammonia (60:30:10 by volume): Rf=0.20.

n-propanol/methanol/water/11 N ammonia/acetic acid (30:30:20:5:15 by volume): Rf=0.35.

n-butanol/acetone/water/acetic acid/11 N ammonia (35:25:21:15:4 by volume)i Rf=0.25.

n-butanol/methanol/water/11 N ammonia (50:25:25:5 by volume): Rf=0.25.

Fixing on carriers:

32232 RP can be fixed on various carriers from which it can be eluted:

| Carrier | Eluant |
| --- | --- |
| cationic resin (for example in the $Na^+$ form) | sodium hydroxide solution (pH 11) at a temperature of between 20° and 100° C. |
| anionic resin (in the $OH^-$ form) : for example Dowex 1 × 2 resin (in the $OH^-$ form) | methanol/water (90:10 by volume) with the addition of 2% of 12N HCl |
| adsorbent resin (for example Amberlite $XAD_2$) | water or methanol/water (10:90 by volume) |

The lactam 35391 RP exhibits the following physical properties:

Appearance: white microcrystalline powder.

Solubility: 35391 RP is soluble in water at the rate of about 10 mg/cc.

The structure of 35391 RP was determined from the following results:

Percentage composition approximately

C=49.6%: H=5.8%: O=17.6%: N=27.0%: theory=C=49.58%: H=5.82%: O=17.61%: N=26.98%.

Potentiometric titration: The potentiometric titration of an aqueous solution of 35391 RP by means of 0.1 M hydrochloric acid shows the presence of a basic group of which the apparent pKa is 7.7. The potentiometric equivalent is about 370.

Figure 5:
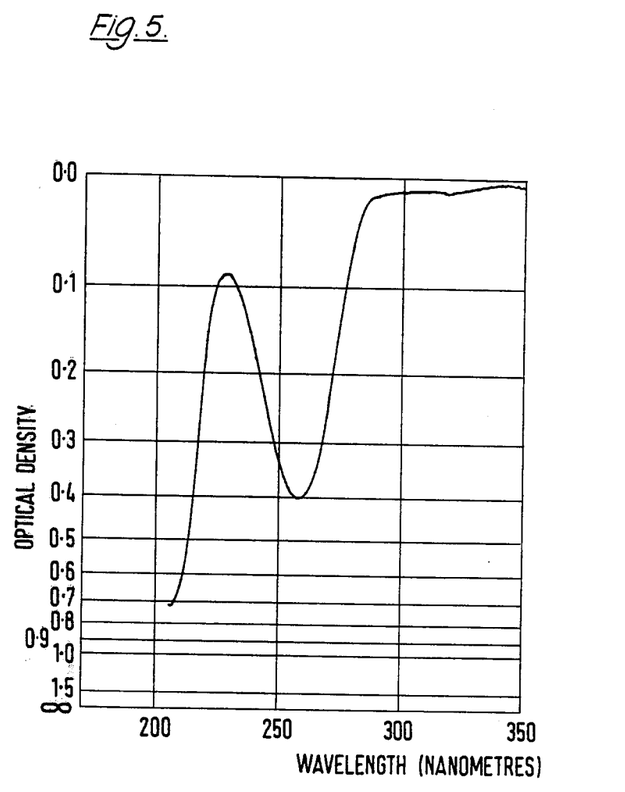

Ultra-violet spectrum: determined using a solution containing 9.8 mg./l. in a phosphate buffer of pH 7 (0.1 M in respect of phosphate ions).

35391 RP shows an absorption maximum at 258 nm ($E_{1\ cm}1\% = 409$).

The spectrum is shown in FIG. 5.

Figure 6:
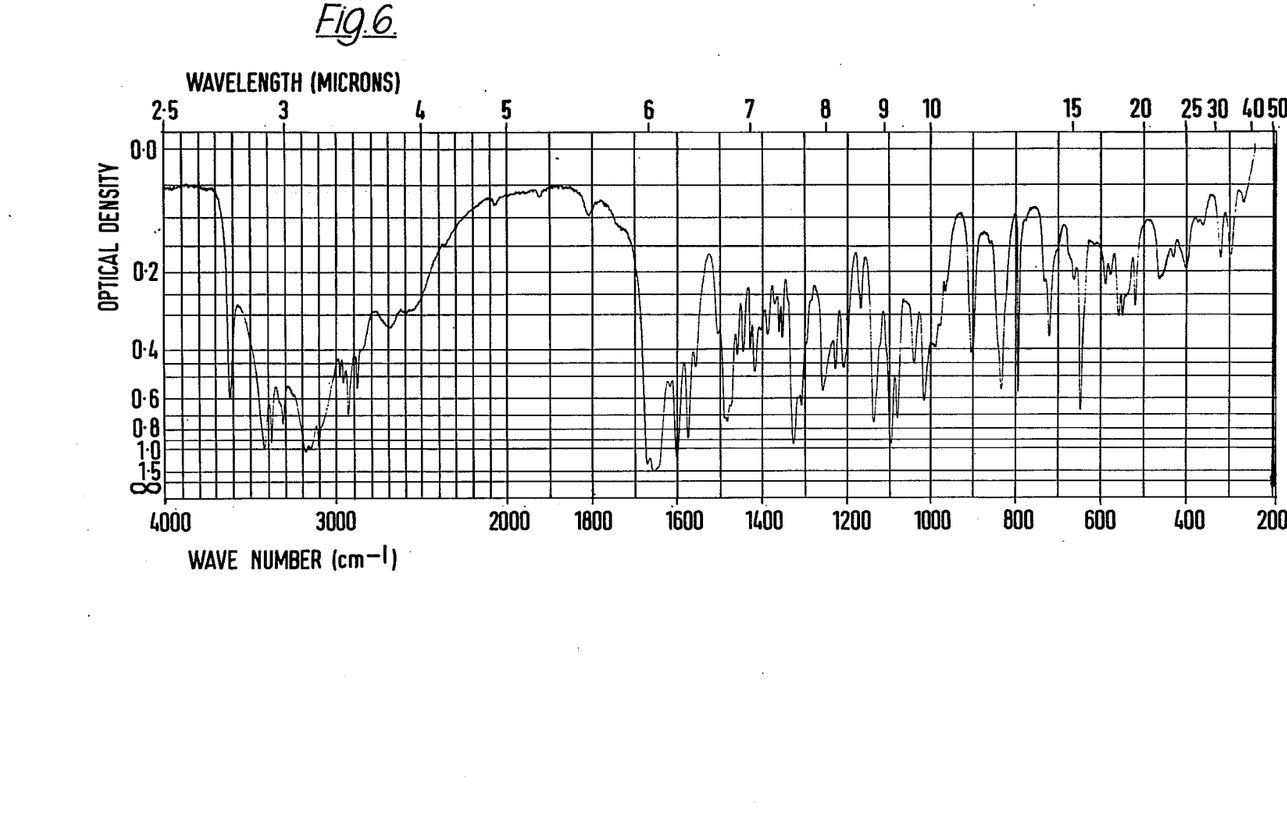

Infra-red spectrum: (determined on tablets of a mixture with KBr).

This spectrum is shown in FIG. 6, in which the abscissae give the wavelengths expressed in microns (upper scale) and the wave numbers in cm$^{-1}$ (lower scale), and the ordinate gives the optical density.

The principal infra-red absorption bands of 35391 RP, expressed in wave numbers (cm$^{-1}$) are given in Table II which follows:

TABLE II

| | | | |
|---|---|---|---|
| 3620 s | 1645 sh | 1210 m | 778 sh |
| 3420 s | 1618 w | 1200 sh | 732 sh |
| 3380 s | 1600 s | 1172 sh | 720 m |
| 3330 sh | 1575 s | 1170 m | 705 sh |
| 3310 m | 1558 m | 1138 s | 675 sh |
| 3250 sh | 1505 m | 1130 sh | 662 m |
| 3180 s | 1488 sh | 1125 sh | 648 s |
| 3150 m | 1482 s | 1105 sh | 640 sh |
| 3100 m | 1472 sh | 1095 s | 615 vw |
| 3080 sh | 1460 m | 1080 s | 590 m |
| 2980 m | 1445 m | 1060 sh | 578 w |
| 2960 m | 1430 m | 1040 m | 560 m |
| 2930 m | 1418 m | 1015 s | 550 m |
| 2880 m | 1402 w | 1010 sh | 540 sh |
| 2850 sh | 1388 m | 990 w | 520 m |
| 2680 m | 1370 w | 980 sh | 462 m |
| 2595 w | 1360 m | 968 m | 455 sh |
| 2550 sh | 1352 m | 962 sh | 430 w |
| 2370 sh | 1340 sh | 905 s | 400 m |
| 2070 vw | 1328 s | 900 sh | 372 vw |
| 1925 vw | 1315 sh | 862 vw | 360 w |
| 1810 w | 1308 m | 840 sh | 325 sh |
| 1740 sh | 1298 sh | 835 s | 320 m |
| 1670 s | 1285 sh | 825 sh | 295 m |
| 1655 vs | 1230 m | 795 s | | vs = very strong
s = strong
m = medium
w = weak
vw = very weak
sh = shoulder

Figure 7:
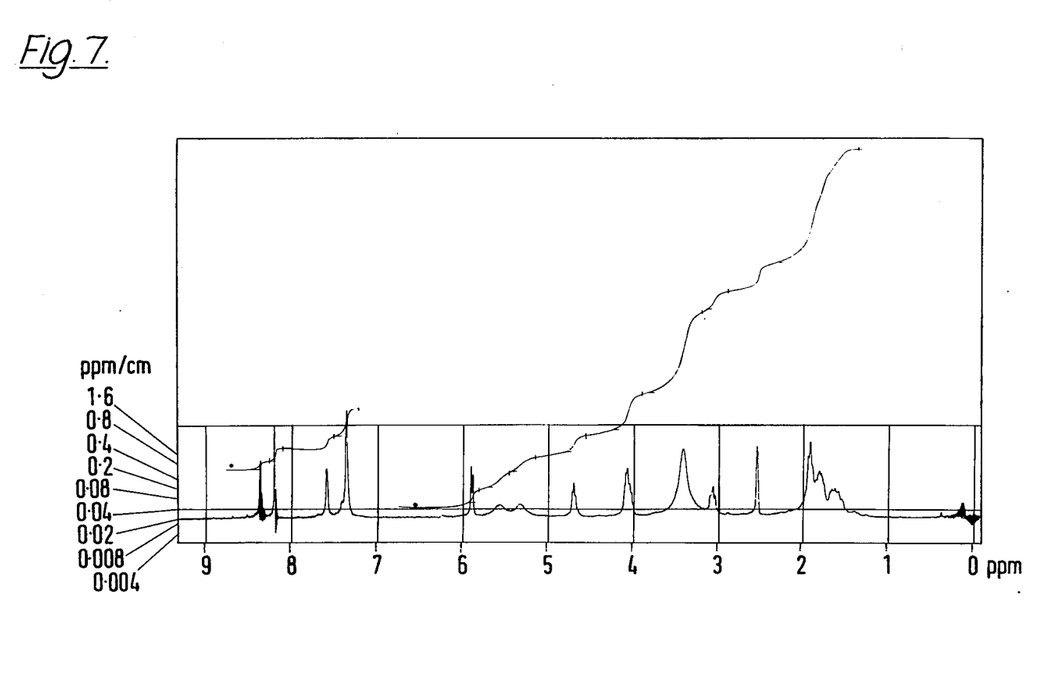

Nuclear magnetic resonance spectrum of the proton in hexadeuterated dimethylsulphoxide: This spectrum, which is shown in FIG. 7, was recorded on a CAMECA TSN-250 spectrometer at a frequency of 250 MHz, using a solution of 44 mg/cc in hexadeuterated dimethylsulphoxide. It exhibits the following characteristics (the chemical shifts are counted positively in p.p.m. towards the weak fields, relative to TMS taken as the internal standard).

| Chemical shift in p.p.m. relative to TMS | Form of the signal, coupling constant (J) and number of protons |
|---|---|
| 1.3 to 2.05 | multiplet (6H) |
| 2.52 | quintuplet |
| 3.05 | multiplet (1H) |
| 3.3 to 3.5 | hump (5H) |
| 4.0 to 4.15 | multiplet (2H) |
| 4.68 | triplet, J = 4.8 Hz (1H) |
| 5.32 | broad singlet (1H) |
| 5.56 | broad singlet (1H) |
| 5.88 | doublet, J = 4.8 Hz (1H) |
| 7.36 | broad singlet (2H) |
| 7.58 | broad singlet (1H) |
| 8.18 | singlet (1H) |
| 8.35 | singlet (1H) |

This spectrum shows that 35391 RP contains 14 non-exchangeable protons.

Nuclear magnetic resonance spectrum of $^{13}$C in hexadeuterated dimethylsulphoxide: This spectrum was recorded on a WH 90 Bruker spectrometer at a frequency of 22.63 MHz using a solution of 135 mg/cc in hexadeuterated dimethylsulphoxide. It exhibits the following characteristics (the chemical shifts in the absence of TMS are measured positively towards the weak fields relative to the hexadeuterated dimethylsulphoxide taken as the internal standard at 39.5 p.p.m. from TMS, and in the Table which follows these shifts are expressed in p.p.m. relative to TMS taken as zero).

| Chemical shift in p.p.m. relative to TMS | Form of the signal in the spectrum recorded in "off-resonance" |
|---|---|
| 25.8 | triplet |
| 26.2 | triplet |
| 40.0 | triplet |
| 48.8 | doublet |
| 50.6 | doublet |
| 72.8 | doublet |
| 73.7 | doublet |
| 80.9 | doublet |
| 87.9 | doublet |
| 119.0 | singlet |
| 139.8 | doublet |
| 148.9 | singlet |
| 152.3 | doublet |
| 155.7 | singlet |
| 173.3 | singlet |

This spectrum shows that 35391 RP contains 15 carbon atoms, namely 4 quaternary carbon atoms, 8 tertiary carbon atoms and 3 secondary carbon atoms.

Mass spectrum: In electron impact mass spectrometry, the molecular peak of empirical formula $C_{15}H_{21}N_7O_4$ is obtained (value found: 363, 1666; value calculated 363, 1655).

The characteristic fragments of the molecule of 35391 RP are:

-$C_{12}H_{16}N_5O_3$ (value found:278, 1247; value calculated 278, 1253)

-$C_{10}H_{16}N_2O_4$ (value found:228, 1102; value calculated 228, 1110)

-$C_7H_8N_5O$ (value found:178, 0729; value calculated 178, 0729)

-$C_5H_5N_5$ (value found:135, 0546; value calculated 135, 0545)

Chromatographic migrations: 35391 RP can be characterised by ascending chromatography on a thin layer of fluorescent (254 nm) silica gel, using various mixtures of solvents and examining the chromatogram at 254 nm after development. The development mixtures are:

methanol/1,2-dichloroethane/11 N ammonia (60:30:20 by volume): Rf=0.7.

n-propanol/methanol/water/11 N ammonia/acetic acid (30:30:20:5:15 by volume): Rf=0.6.

n-butanol/acetone/water/11 N ammonia/acetic acid (35:25:21:4:15 by volume): Rf=0.5.

32232 RP and 35391 RP are generally devoid of bacteriostatic activity towards bacteria.

Toxicity: In mice, 32232 RP exhibits a 50% lethal dose (LD$_{50}$) greater than 1000 mg/kg animal body weight when administered orally, and 35391 RP is non-toxic at a dose of 1000 mg/kg animal body weight when administered orally or subcutaneously.

Anti-fungal activity in vitro: The anti-fungal activity of 32232 RP and of 35391 RP towards a certain number of fungi has been determined by one of the dilution methods usually employed for this purpose. For each fungus, the smallest concentration of active substance which, under defined conditions, causes 95 to 100% inhibition of the fungus (AC $_{95-100}$) was determined. The results of the various determinations are summarised in Table III below, where the minimum active concentrations are expressed in micrograms of substance per cc. of test medium.

TABLE III

| Test Fungi | Minimum active concentration in µg./cc | |
|---|---|---|
| | 32232 RP | 35391 RP |
| Candida albicans Pa 1 | 3 | 40 |
| Candida albicans IP 200 | 5 | 70 |
| Candida albicans Hi 7 | 5 | 75 |
| Candida krusei IP 208 | 4 | 60 |
| Hansenula anomala | 2 | 35 |
| Blastomyces dermatitidis | 5 | 60 |
| Saccharomyces pastorianus | 0.3 | 7 |
| Saccharomyces ellipsoideus | 0.9 | 15 |
| Saccharomyces cerevisiae | 0.3 | 10 |
| Microsporum canis | >500 | 300 |
| Microsporum rubrum | >500 | 300 |
| Epidermophyton floccosum | >500 | 250 |
| Trichophyton mentagrophytes | >500 | 350 |
| Aspergillus niger | >500 | >500 |
| Aspergillus fumigatus | >500 | >500 |
| Rhizopus nigricans | >500 | >500 |
| Mucor corymbifer | >500 | >500 |
| Fusarium oxysporum | >500 | >500 |
| Botrytis cinerea | >500 | >500 |
| Penicillium digitatum | 15 | 25 |

Anti-fungal activity in vivo

Against generalised candidosis, caused by *Candida albicans*, in mice, 32232 RP and 35391 RP have proved particularly active when administered orally or subcutaneously at doses of between 25 mg/kg animal body weight and 200 mg/kg animal body weight per day for 4 consecutive days.

32232 RP can be obtained from appropriate culture media of a new microorganism (identified more completely hereafter), belonging to the genus Streptomyces and designated by the name *Streptomyces incarnatus* DS 26068.

The microorganism which produces the anti-fungal agent is a strain of Streptomyces which has been isolated from a sample of soil taken in India, and which has been given the number DS 26068. This organism has been deposited at the Northern Regional Research Laboratory of the U.S. Department of Agriculture in Peoria, Illinois (United States), where it has been registered under the number NRRL 8089. Samples can be provided by this laboratory to any person referring to the publication of the present document.

The isolation of the microorganism was carried out following the general method which consists of suspending a small amount of soil in sterile distilled water, diluting the suspension to various concentrations and spreading a small volume of each dilution on the surface of Petri dishes containing a nutrient agar medium. After incubation for several days at 26° C., which allows the microorganisms to develop, the colonies which it is desired to isolate in order to study them further are taken and transplanted onto nutrient agar slopes in order to obtain more abundant cultures thereof.

*Streptomyces incarnatus* DS 26068 forms oval to cylindrical spores with rounded ends, measuring about 0.8 to 1.0 µ/0.4 to 0.5 µ. Its sporophores are in clusters. In general, its chains of spores are long, comprising up to several tens of spores, and show a certain degree of polymorphism, some of the spores being straight or more or less flexuous, whilst others bend over in the form of a hook or even coil up, describing a more or less open spiral with one and occasionally several turns. According to its mode of sporulation, *Streptomyces incarnatus* DS 26068 falls into the *Retinaculum Apertum Section* of the Pridham classification.

*Streptomyces incarnatus* DS 26068 develops well at 26° C. and at 37° C., but not at 50° C. It has a sporulated aerial mycelium of light pink colour.

The colouration of its vegetative mycelium ranges, depending on the media, from brown-yellow or yellow-brown to very deep brown. In general it shows rather abundant production of a melanin pigment on organic media, and in particular on Waksman special tyrosine-yeast extract agar (melanin formation medium); on synthetic agar media it most frequently produces a soluble pigment which is of a more or less deep brown depending on the case.

In its cultures, carried out at 26° C., it exhibits the following biochemical characteristics:

| | |
|---|---|
| Production of melanin | : positive |
| Production of H$_2$S | : positive |
| Tyrosinase | : positive |
| Liquefaction of gelatin | : negative |
| Utilisation of cellulose | : negative |
| Production of nitrites from nitrates | : positive, weak |
| Hydrolysis of starch | : positive |
| Culture on skimmed milk | : peptonisation without coagulation |

The cultural characteristics of *Streptomyces incarnatus* DS 26068 are summarised in Table IV hereafter. These are the characteristics of cultures which have reached a good stage of development, that is to say have been at 26° C. for about 2 to 3 weeks, unless stated otherwise. These characteristics were observed on nutrient agars and broths usually employed to determine the morphological characteristics of the strains of Streptomyces, the cultures on agar media being carried ot on sloping agars. A certain number of the culture media employed were prepared in accordance with the formulations indicated in "The Actinomycetes", S. A. Waksman, p. 193–197, Chronica Botanica Company, Waltham, Mass., U.S.A., 1950; in this case they are indicated by the letter W followed by the number which has been given to them in "The Actinomycetes". The references or compositions of the other culture media are as follows:

Ref. A: "Hickey and Tresner's Agar"—T. G. Pridham et al.—Antibiotics Annual, 1956–1957, p. 950.

Ref. B: "Bennett's Agar"—S. A. Waksman—The Actinomycetes vol. 2, p. 331, No. 30; The Williams and Wilkins Company, Baltimore 1961.

Ref. C: Formula W-23, with the addition of 2% of agar.

Ref. D: "Yeast Extract Agar"—T. G. Pridham et al.—Antibiotics Annual, 1956–1967, p. 950.

Ref. E: "Tomato Paste Oatmeal Agar"—T. G. Pridham et al.—Antibiotics Annual, 1956–1957, p. 950.

Ref. F: "Melanin formation medium"—The Actinomycetes, vol. 2, p. 333, No. 42—S. A. Waksman—The Williams and Wilkins Company, Baltimore, 1961.

Ref. G: W. E. Grundy et al.—Antibiotics and Chem. 2, 401, 1952.

Ref. H: "Inorganic Salts—Starch Agar"—T. G. Pridham et al.—Antibiotics Annual, 1956-1957, p. 951.

Ref. I: W. E. Grundy et al.—Antibiotics and Chem. 1,30, 1951.

Ref. J: corresponds to formula W-1, with 30 g of sucrose replaced by 15 g of glucose.

Ref. K: corresponds to formula W-1, with 30 g of sucrose replaced by 15 g of glycerol.

Ref. L: corresponds to formula W-18, with 30 g of sucrose replaced by 15 g of glucose.

Ref. M: corresponds to formula W-18, with the sucrose omitted and replaced by small strips of filter paper partially immersed in the liquid.

Ref. N: "Manual of Methods for Pure Culture Study of Bacteria" of the Society of American Bacteriologists, Geneva, N.Y., $II_{50}$-18.

Ref. P: "Plain Gelatin"—prepared in accordance with the instructions in the "Manual of Methods for Pure Culture Study of Bacteria" of the Society of American Bacteriologists, Geneva, N.Y., $II_{50}$-18.

Ref. Q: Skimmed milk in the form of a commercially available powder, reconstituted in accordance with the manufacturer's instruction.

Ref. R: Medium given for investigation of the production of $H_2S$, by: H. D. Tresner and F. Danga—Journal of Bacteriology, 76, 239-244, 1958.

TABLE IV

| Culture medium | Degree of development | Vegetative mycelium (v.m.) or underside of the culture | Aerial structure (comprising the combination of the aerial mycelium (a.m.) and of the sporulation) | Soluble pigment | Observations and biochemical properties |
|---|---|---|---|---|---|
| Hickey and Tresner agar (Ref. A) | good | underside very deep brown | whitish to greyish pink; well developed | block brown | Oval to cylindrical Spores, with rounded ends, measuring 0.8 to 1.0 $\mu$/0.4 to 0.5 $\mu$. Sporophores in clusters. Chains of spores straight or flexuous, or curved to form a hook, or forming a more or less open spiral having from 1 to several turns. |
| Bennett agar (Ref. B) | good | underside yellow brown | whitish; medium development | yellow brown | |
| Emerson agar (Ref. C) | good | underside yellow brown | white; moderately developed | deep brown | |
| Pridham yeast extract agar (Ref. D) | good | underside yellow brown | whitish to light greyish pink; medium development | blackish brown | |
| Pridham oatmeal and tomato extract agar (Ref. E) | good | underside yellow brown | whitish to light greyish pink; well developed | deep brown | |
| Glucose-peptone agar (W-7) | rather good | v.m. yellow brown | whitish; very poorly developed | blackish brown | |
| Nutrient agar (W-5) | moderate | v.m. yellow brown | none | deep yellow brown | |
| Tyrosine-yeast extract agar for the formation of melanin (Ref. F) | rather poor | v.m. very deep brown | none or greyish; in the form of traces | black | Production of melanin: positive (readings taken in accordance with the recommendations of the author) |
| Krainsky calcium malate agar (Ref. G) | very poor | v.m. colourless to greyish; very poorly developed | none | none | Solubilisation of the malate : positive but weak and very slow |
| Ovalbumin agar (W-12) | very moderate | v.m. yellow brown | pink grey; poorly developed | weak brownish grey | - |
| Glucose-asparagine agar (W-2) | rather good | underside brown yellow to deep brown | whitish to light greyish pink; rather well developed | yellow brown | |
| Glycerol-asparagine agar (W-3) | rather good | v.m. yellow brown | greyish white; in the form of traces | yellow brown | |
| Pridham starch-mineral salts agar (Ref. H) | good | underside light yellow brown | whitish to greyish pink; rather well developed | weak greyish brown | Hydrolysis of the starch: positive Spores oval to cylindrical with rounded ends, measuring 0.8 to 1.0 $\mu$/ 0.4 to 0.5 $\mu$. Sporo- |

TABLE IV-continued

| Culture medium | Degree of development | Vegetative mycelium (v.m.) or underside of the culture | Aerial structure (comprising the combination of the aerial mycelium (a.m.) and of the sporulation) | Soluble pigment | Observations and biochemical properties |
|---|---|---|---|---|---|
| | | | | | phores in clusters. Chains of spores straight or flexuous, or curved to form a hook, or forming a more or less open spiral having from 1 to several turns. |
| Starch agar (W-11) | moderate | underside light brown, slightly pink | greyish pink; well developed | weak pink grey | |
| Grundy starch and (NH4)2HPO4 agar (Ref. I) | rather good | underside yellow brown | greyish pink; well developed | weak brownish | |
| Czapek synthetic agar with sucrose (W-1) | medium | underside yellowish brown | greyish white: in the form of traces | weak brownish | |
| Czapek synthetic agar with glucose (Ref. J) | medium | underside yellow brown | greyish white; in the form of traces | weak greyish yellow brown | |
| Czapek synthetic agar with glycerol (Ref. K) | medium | v.m. yellow brown yellow | none or whitish; in the form of traces | yellow brown | |
| Starch-nitrate broth (W-19) | rather good | brownish velum | white; very moderately developed | none or very weak brownish | Production of nitrites: positive, weak |
| Czapek glucose broth (Ref. L) | very moderate | whitish flocculent | none | none | Production of nitrites: positive, weak |
| Czapek cellulose broth (Ref. M) | none | | | | Utilisation of cellulose: negative |
| Nitrate nutrient broth (Ref. N) | poor | poorly developed brownish ring | none | very deep brown | Production of nitrites: doubtful |
| Culture on potato (W-27) | rather good | v.m. greyish to deep chestnut | none, or whitish; very weakly developed | black | |
| 12% pure gelatine (Ref. P) | medium | v.m. deep brown | none | black brown | No liquefaction |
| Skimmed milk (Ref. Q) | good | yellow brown ring | none | — | No coagulation, peptonisation positive |
| Tresner and Danga agar (Ref. R) | moderate | v.m. very deep brown | none | black | Production of H2S: positive (readings taken in accordance with the recommendations of the authors) |

The ability of *Streptomyces incarnatus* DS 26,068 to utilise various sources of carbon and of nitrogen to ensure its development was determined in accordance with the principle of the method of Pridham and Gottlieb (J. of Bact. 56, 107–114, 1948); the degree of development was observed, after a suitable period of incubation at 25° C., on the base medium indicated by the authors, replacing either the glucose by the various sources of carbon respectively tested, or $(NH_4)_2 SO_4$ by the various sources of nitrogen respectively tested. The results are indicated in Table V.

TABLE V

| Sources of carbon tested | Utilisation | Sources of nitrogen tested | Utilisation |
|---|---|---|---|
| D - ribose | slight and slow | $NaNO_3$ | positive |
| D - xylose | positive | $NaNO_2$ | positive |
| L - arabinose | positive | $(NH_4)_2SO_4$ | positive |
| L - rhamnose | positive | $(NH_4)_2HPO_4$ | positive |
| D - glucose | positive | urea | positive |
| D - galactose | positive | L - asparagine | positive |
| D - fructose | positive | glucosamine | positive |
| D - mannose | positive | glycine | positive |
| L - sorbose | negative | sarcosine | negative |
| lactose | positive | DL - alanine | positive |

TABLE V-continued

| Sources of carbon tested | Utilisation | Sources of nitrogen tested | Utilisation |
|---|---|---|---|
| maltose | positive | DL - valine | positive |
| sucrose | positive | DL - aspartic acid | positive |
| trehalose | positive | DL - glutamic acid | positive |
| cellobiose | positive | L - arginine | positive |
| raffinose | positive | L - lysine | positive |
| dextrin | positive | DL - serine | positive |
| inulin | negative | DL - threonine | positive |
| starch | positive | DL - methionine | negative |
| glycogen | positive | taurine | negative |
| glycerol | positive | DL - phenylalanine | positive |
| erythritol | negative | L - tyrosine | positive |
| adonitol | negative | DL - proline | positive |
| dulcitol | negative | L - hydroxyproline | positive |
| D - mannitol | positive | L - histidine | positive |
| D - sorbitol | negative | L - tryptophan | positive |
| inositol | positive | betaine | positive |
| salicin | negative | | |

*Streptomyces incarnatus* DS 26068 exhibits a combination of characteristics which does not coincide exactly with any of those of the strains already described, and it is for this reason that it must be considered as a new species.

Considering the species described in "The Actinomycetes" (Vol. 2, S. A. Waksman, The Williams and Wilkins Company, Baltimore, 1961), as well as in Bergey's Manual of Determinative Bacteriology (seventh edition, the Williams and Wilkins Company, Baltimore, 1957), the species to which *Streptomyces incarnatus* DS 26068 comes closest is *Streptomyces venezuelae* which, like the former, produces melanin pigments on organic media, has a vegatative mycelium ranging from yellow to brown depending on the culture media, and has a sporulated aerial mycelium of pink colour. However, it must be distinguished from this species, from which it is separated by a number of differences which are indicated in Table VI hereafter.

TABLE VI

| | *Streptomyces incarnatus* DS 26068 | *Streptomyces venezuelae* (The Actinomycetes, Vol. 2, p. 280-281, S. A. Waksman) |
|---|---|---|
| Mode of sporulation (section in the Pridham classification) | Retinaculum Apertum | Rectus Flexibilis |
| Utilisation of: | | |
| sucrose | positive | negative |
| raffinose | positive | negative |
| mannitol | positive | negative |
| inositol | positive | negative |
| salicin | negative | positive |
| Liquefaction of gelatin | none | rapid |
| Calcium malate agar | v.m. poor, colourless to greyish; a.m. none | v.m. yellow to brown a.m. grey |
| Sucrose-nitrate agar (Czapek) | a.m. greyish white; in the form of traces | a.m. light lavender |
| Nutrient agar | a.m. none | a.m. grey |
| Potato | a.m. none or whitish; very slightly developed | a.m. grey | v.m. = vegetative mycelium
a.m. = aerial mycelium

According to a feature of the invention, the α,δ-diaminoacid 32232 RP is produced by aerobically cultivating *Streptomyces incarnatus* DS 26068, or a mutant thereof capable of producing 32232 RP, in an aqueous medium containing assimilable sources of carbon, nitrogen and inorganic substances, and isolating from the medium 32232 RP formed during the culture.

The culture of *Streptomyces incarnatus* DS 26068 can be carried out by any of the known aerobic surface or submerged culture methods, but the latter are preferred for reasons of convenience. For this purpose, the various types of apparatus which are currently employed in the fermentation industry may be used.

In particular, the following sequence of operations may be adopted:

*Streptomyces incarnatus* DS 26068 - stock
↓
culture on agar
↓
culture in a shaken flask
↓
inoculum culture in a fermenter
↓
production culture in a fermenter The fermentation medium must essentially contain an assimilable source of carbon and an assimilable source of nitrogen and inorganic substances, in particular chlorides, and optionally growth-promoting factors; all these ingredients may be supplied in the form of well-defined products or in the form of complex mixtures, such as those found in biological products of various origins.

As sources of assimilable carbon there may be used carbohydrates such as glucose, sucrose, maltose, dextrins, starch or other carbon-containing substances such as sugar alcohols, e.g. glycerol, or certain organic acids, e.g. lactic or citric acid. Certain animal or vegetable oils such as lard oil or soya bean oil may be advantageously used instead of, or in admixture with, the aforementioned substances.

The suitable sources of assimilable nitrogen are extremely varied. They may be very simple chemical compounds such as inorganic or organic ammonium salts, urea or certain aminoacids. They may also be complex substances containing principally nitrogen in a protein form, e.g. casein, lactalbumin, gluten and their hydrolysates, soya bean flour, groundnut meal, fishmeal, meat extract, yeast extract, distiller's solubles and corn-steep liquor.

Amongst the inorganic constituents added, some may have a buffering or neutralising effect, such as the alkali metal or alkaline earth metal phosphates or calcium carbonate or magnesium carbonate. Others contribute to the ionic equilibrium necessary for the development of *Streptomyces incarnatus* DS 26068 and for the production of 32232 RP, such as the alkali metal and alkaline earth metal chlorides and sulphates. Some of them act more especially as activators of the metabolism of *Streptomyces incarnatus* DS 26068, e.g. the salts of zinc, cobalt, iron, copper and manganese.

Suitable growth-promoting factors are products of a vitamin nature, e.g. riboflavin, folic acid and pantothenic acid.

The pH of the fermentation medium at the start of the culture should preferably be between 5.8 and 7.8, and more preferably between 6.2 and 7.4. The optimum fermentation temperature is from 25° to 30° C., but satisfactory production is achieved at temperatures between 23° and 33° C. The rate of aeration of the fermentation medium may vary within quite wide limits, but it has been found that aeration rates of 0.3 to 3 liters of air per liter of medium per minute are particularly suitable. The maximum yield of 32232 RP is obtained after 2 to 8 days' culture, but this period depends predominantly on the medium used.

32232 RP can be isolated from the fermentation medium in the following manner:

The fermentation medium can be filtered in the presence of a filtration agent, at a pH which is generally that of the medium at the end of the production phase.

32232 RP, which is present in the filtrate and in the washing liquors of the filter cake, is then fixed on a carrier which can consist of a cationic or anionic resin or an adsorbent resin.

The antifungal agent 32232 RP is then isolated from its carrier by washing the latter by means of a suitable eluent, such as water or water to which an electrolyte or a water-miscible solvent has been added.

32232 RP can thereafter be precipitated from its solution by adding the latter to a poor solvent for it such as acetone or a methanol-acetone mixture.

32232 RP thus obtained can optionally be purified by filtration or by fixing on various carriers, these fixing operations being followed by elutions with suitable eluents and precipitations by means of a water-soluble poor solvent or non-solvent for the anti-fungal agent.

35391 RP can be obtained by heating 32232 RP in an organic solvent such as an aromatic hydrocarbon, at a temperature between 80° C. and the reflux temperature of the reaction mixture, the water formed being removed by azeotropic distillation. Preferably, toluene is used as the organic solvent.

32232 RP and 35391 RP (obtained in accordance with the process of the present invention) can optionally be converted into addition salts with acids in accordance with methods known per se.

Alkali metal and alkaline earth metal salts of 32232 RP can also be obtained from the α,δ-diaminoacid by methods known per se. By the term "methods known per se" as used in this specification is meant methods heretofore used or described in the literature.

The following Examples illustrate the preparation of 32232 RP and its lactam 35391 RP.

The activity of the mixtures containing 32232 RP is determined by means of the microbiological diffusion method, using *Saccharomyces ellipsoideus* as the sensitive microorganism, and relative to 32232 RP of strength 1000 μg./mg. This activity is expressed in μg./mg. for the solids and in μg./cc for the solutions.

EXAMPLE 1

(A) Fermentation

Peptone (1200 g), yeast extract (600 g), sodium chloride (600 g) and tap water (sufficient to make up to 107 liters) are introduced into a 170 liter fermenter.

The pH is 7.0. The medium is sterilised by bubbling steam at 122° C. through it for 40 minutes. After cooling, the volume of the broth is 117 liters because of the condensation of steam during the sterilisation; the volume is made up to 120 liters by adding a sterile aqueous solution (3 liters) which contains glucose monohydrate (1200 g).

The pH of the medium is 7.0. The medium is then inoculated with a culture (200 cc), produced in an agitated Erlenmeyer flask, of *Streptomyces incarnatus* DS 26068. The culture is developed at 30° C. for 26 hours whilst agitating and aerating with sterile air; it is then suitable for inoculation of the production culture.

The production culture is carried out in an 800 liter fermenter containing the following materials: corn-steep liquor (containing 50% solids; 10 kg), glucose monohydrate (5 kg), soya bean oil (10 liters), cobalt chloride hexahydrate (0.015 kg) and tap water (sufficient to make up to 465 liters).

The pH of the medium is adjusted to 6.40 by adding 10N sodium hydroxide solution (700 cc) and calcium carbonate (2.5 kg) is then added.

The pH of the medium is now 6.50. The broth is sterilised by bubbling steam at 122° C. through it for 40 minutes. After cooling, the volume of the broth is 500 liters because of the condensation of steam during the sterilisation. The pH of the medium is 6.85.

It is then inoculated with the inoculum culture (50 liters) produced in the 170 liter fermenter, described above. The culture is developed at 30° C. for 90 hours with agitation using a stirrer rotating at 160 revolutions per minute and aeration with sterile air (30 m$^3$/hr). At the end of the operation, the pH of the culture medium is 8.00 and the volume of the broth is 480 liters. The production of 32232 RP is 36 μg/cc.

(B) Extraction

The must (880 liters), obtained as indicated above, having an activity of 30 μg/cc is filtered on a filter press with the aid of a filtration aid (45 kg). The filter cake is washed on the filter with water (200 liters).

The filtrate and the wash liquor are combined and chromatographed on a column containing "Amberlite IR 120" cationic resin (40 liters) in the Na$^+$ form. The resin is washed on the column with distilled water (120 liters). The effluent and the wash liquor are discarded.

The resin is taken up in water (200 liters) whilst stirring and the pH is adjusted to 11 by addition of 6N sodium hydroxide solution (1 liter).

The resin is stirred for about 30 minutes at 90° C. and then filtered off and washed on the filter with distilled water (50 liters) at a temperature of about 20° C.

The eluate and the wash liquor are combined and the pH is adjusted to 6 by adding 6N hydrochloric acid (580 cc.). The solution is concentrated under reduced pressure (5 to 10 mm Hg) to a volume of 1 liter.

Methanol (6 liters) is then added and the 32232 RP is precipitated by pouring the solution into acetone (60 liters) whilst stirring. The precipitate is filtered off, washed on the filter with acetone (2 liters) and dried under reduced pressure at 35° C.

Crude 32232 RP (175 g), having an activity of 110 µg/mg, is thus obtained.

(C) Purification

The crude product obtained as described above (175 g) is dissolved in water (1 liter). The insoluble matter is filtered off. The solution is chromatographed on a column containing "Amberlite IR 120" cationic resin (3 liters) in the Na+ form. The resin is washed on the column with distilled water (3 liters). The resin is suspended in water (3 liters) adjusted to pH 11 by addition of 6N sodium hydroxide solution (30 cc). The suspension is stirred for 30 minutes at 90° C. and then filtered. A first eluate is obtained.

The resin is taken up under the same conditions to give a second eluate.

The two eluates are combined, neutralised to pH 7 by addition of 6N hydrochloric acid (50 cc) and concentrated under reduced pressure to a volume of 900 cc. This concentrate is passed through a column containing "Amberlite XAD2" resin (800 cc). The resin is washed on the column with water (5 liters), the effluent and the wash liquor being collected in fractions of 250 cc.

Fractions 1 to 10 are combined and then concentrated under reduced pressure to a volume of 110 cc.

Methanol (300 cc) is added and the 32232 RP is precipitated by slowly pouring the solution into acetone (800 cc) whilst stirring.

The precipitate is filtered off, washed on the filter with acetone (100 cc) and dried under reduced pressure (5 mm Hg) for 15 hours at 35° C.

32232 RP (27.2 g), having an activity of 411 µg/mg, is thus obtained.

This product is dissolved in water (300 cc) and the solution is chromatographed on a column containing "Amberlite IRC 50" cationic resin (1 liter) in the $NH_4^+$ form. The resin is washed with water (1 liter).

Elution is carried out with a linear water/0.2N ammonia gradient (1:1 by volume, 6 liters).

The effluent, the wash liquor and the eluate are collected in fractions of 250 cc. The active fractions are selected by measuring the optical density at 260 nm. Fractions 17 to 21 are combined and concentrated under reduced pressure to a volume of 70 cc. The concentrate is diluted by adding methanol (70 cc) and the 32232 RP is precipitated by slowly pouring this concentrate into acetonitrile (500 cc) whilst stirring. The precipitate is filtered off, washed on the filter with acetone (50 cc) and dried under reduced pressure (5 mm Hg) for 15 hours at 35° C.

32232 RP (10.5 g), having an activity 812 µg/mg, is obtained.

32232 RP (10 g) obtained as just described above is dissolved in water (100 cc) and passed through a column containing "Sephadex G 25" dextran gel (1 kg) swollen in water. Elution is carried out with water. The effluent and the eluate are collected in fractions of 20 cc. The active fractions are selected by measuring the optical density at 260 nm. The 220 first fractions (4400 cc) are discarded and the next 53 fractions (1060 cc) are concentrated under reduced pressure to a volume of 120 cc. The solution is lyophilised. Pure 32232 RP (6.94 g) is thus obtained.

EXAMPLE 2

32232 RP (2 g) is suspended in toluene (250 cc) and the mixture is then heated under reflux, with constant stirring, for 76 hours whilst removing the water, at the rate at which it is formed, by azeotropic distillation and re-cycling the toluene. After cooling to a temperature of about 20° C., the product in suspension is filtered off and then dried under reduced pressure (15 mm Hg) at 35° C. for 15 hours. A product (1.8 g) is thus obtained, which is dissolved in water (5 cc) heated to 60° C. After cooling at +5° C. for 48 hours, the crystals which have appeared are filtered off, washed with distilled water (1 cc) and then dried under reduced pressure (5 mm Hg). Crystalline 35391 RP (0.95 g) is thus obtained.

The present invention also includes within its scope medicinal compositions which comprise at least one of the antifungal agents 32232 RP and 35391 RP or a non-toxic acid addition salt thereof or a non-toxic alakli metal or alkaline earth metal salt of 32232 RP, in association with any other compatible product, whether it be inert or physiologically active. The compositions can be administered orally, parenterally or rectally or used topically. They usually contain from 99.9% to 0.01% of 32232 RP and/or 35391 RP.

Solid compositions for oral administration include tablets, pills, powders or granules. In such compositions, the active product according to the invention is mixed with one or more inert diluents or adjuvants such as sucrose, lactose or starch. The solid compositions may also comprise additional substances other than inert diluents, for example lubricant agents such as magnesium stearate.

Liquid compositions for oral administration include pharmaceutically acceptable solutions, suspensions, emulsions, syrups and elixirs containing inert diluents such as water or liquid paraffin. These liquid compositions may also contain substances other than inert diluents, for example wetting agents, sweeteners or flavourings.

Compositions for parenteral administration may be sterile aqueous or non-aqueous solutions, suspensions or emulsions. As the solvent or vehicle there may be used propylene glycol, polyethylene glycol, vegetable oils, in particular olive oil, and organic injectable esters, for example ethyl oleate. These compositions can also contain adjuvants, in particular wetting agents, emulsifiers or dispersing agents. Sterilisation can be carried out in various ways, for example by means of a bacteria-retaining filter, by incorporating sterilising agents into the composition, by irradiation or by heating. They can also be prepared in the form of sterile solid compositions which can be dissolved, at the time of use, in sterile water or in any other injectable sterile medium.

The compositions for rectal administration are suppositories which, in addition to the active product, can contain excipients such as cacao butter or suppositories wax.

The compositions for topical treatment can be in the form of lotions, ointments, creams, milks, powders or aerosols. These compositions can furthermore contain additives such as deodorants or antiperspirants.

In these compositions, the content of antifungal agent 32232 RP and/or 35391 RP is generally between 0.01% and 5%.

The lotions are preferably either aqueous lotions or aqueous-alcoholic solutions which contain between 0.01% and 1% by weight of 32232 RP and/or 35391 RP.

The creams and the ointments are emulsions of a mineral, animal or vegetable oil in water, which contain between 0.01% and 5% by weight of antifungal agent 32232 RP and/or of antifungal agent 35391 RP.

The compositions in the form of powders contain between 0.01% and 5% by weight of 32232 RP and/or 35391 RP, preferably mixed with talc and one or more anti-agglomerant agents.

The compositions in the form of aerosols preferably contain an aqueous-alcoholic solution of 32232 RP and/or of 35391 RP and at least one propellant gas which has been compressed or liquefied under pressure.

In human therapy these compositions are particularly active against illnesses caused by yeasts and more especially against candidoses such as buccal and intestinal candidoses, internal mycoses (e.g. pulmonary, sinusal, biliary, urinary or generalised mycoses), cutaneomucosal candidoses and genital infections caused by *Candida albicans*.

In general, the physician will decide the posology which he considers to be the most appropriate in accordance with the age, the weight, the degree of infection and other factors pertaining to the subject to be treated. In general, the doses are between 1 and 10 g per day for oral administration to an adult.

The following Examples illustrate medicinal compositions according to the invention.

EXAMPLE 3

Tablets having the following compositions are prepared in the usual manner:

| | |
|---|---|
| antifungal agent 32232 RP | 0.500 g |
| wheat starch | 0.200 g |
| colloidal silica | 0.045 g |
| magnesium stearate | 0.005 g |

EXAMPLE 4

Tablets having the following composition are prepared in the usual manner:

| | |
|---|---|
| antifungal agent 35391 RP | 0.500 g |
| wheat starch | 0.200 g |
| colloidal silica | 0.045 g |
| magnesium stearate | 0.005 g |

We claim:

1. Process for the production of the α,δ-diaminoacid herein designated 32232 RP corresponding to the formula:

which comprises aerobically cultivating *Streptomyces incarnatus* DS 26068 (NRRL 8089), or a mutant thereof capable of producing 32232 RP, in an aqueous medium containing assimilable sources of carbon, nitrogen and inorganic substances, and isolating from the medium 32232 RP formed during the culture, as such or an internal salt of the said α,δ-diaminoacid, an addition salt of the said α,δ-diaminoacid with a non-toxic pharmaceutically acceptable acid, or an alkali metal or alkaline earth metal salt of the said β,δ-diaminoacid.

2. Process according to claim 1 in which 32232 RP is isolated from the culture medium by filtering the said medium in the presence of a filtration agent, fixing 32232 RP present in the filtrate and in the wash liquors of the filter cake on a carrier consisting of a cationic or anionic resin or an adsorbent resin, eluting 32232 RP from the carrier, and precipitating 32232 RP from its solution so obtained by adding a poor solvent for 32232 RP to cause the crude product to precipitate, and isolating the precipitated 32232 RP.

3. Process according to claim 1 in which the crude 32232 RP obtained is subsequently purified by filtration or by fixing on a carrier, the fixing operation being followed by elution of the 32232 RP from the carrier and precipitation of 32232 RP from the solution so obtained by means of a poor solvent or non-solvent for the 32232 RP."

4. Process according to claim 1 in which the culture is effected under submerged aerobic conditions commencing at a pH between 5.8 and 7.8 and a temperature from 23° to 33° C.

5. Process according to claim 4 in which the pH of the culture medium at the start of the culture is between 6.2 and 7.4.

6. Process according to claim 4 in which the temperature of the culture medium is from 25° to 30° C.

7. Process according to claim 1 in which the culture medium is aerated at a rate of 0.3 to 3 liters of air per liter of medium per minute.

8. Process according to claim 1 in which the culture is continued for 2 to 8 days.

9. Process according to claim 2 in which the poor solvent for 32232 RP is acetone or a methanol-acetone mixture.

10. Process according to claim 1 followed by thep step of converting the α,β-diaminoacid 32232 RP thus obtained into an addition salt with a non-toxic pharmaceutically acceptable acid, or into an alkali metal or alkaline earth metal salt.

* * * * *